(12) United States Patent
Inoue (10) Patent No.: US 8,420,013 B1
(45) Date of Patent: Apr. 16, 2013

(54) TOTAL ORGANIC CARBON MEASUREMENT APPARATUS

(75) Inventor: Shinsuke Inoue, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 13/420,344

(22) Filed: Mar. 14, 2012

(51) Int. Cl.
*G01N 21/00* (2006.01)

(52) U.S. Cl.
USPC .............. 422/62; 210/85; 210/143; 422/80; 436/50; 436/146

(58) Field of Classification Search .............. 422/52, 422/62, 67, 80; 436/50, 146; 210/85, 143
See application file for complete search history.

(56) References Cited

U.S. PATENT DOCUMENTS

| | | | |
|---|---|---|---|
| 5,132,094 A | 7/1992 | Godec et al. | |
| 6,007,777 A * | 12/1999 | Purcell et al. | 422/80 |
| 2006/0196529 A1 * | 9/2006 | Kenowski et al. | 134/56 R |
| 2007/0178022 A1 * | 8/2007 | Bauman et al. | 422/130 |

FOREIGN PATENT DOCUMENTS

| | | |
|---|---|---|
| JP | 10-090134 A | 4/1998 |
| JP | 2000-187027 A | 7/2000 |
| JP | 2006-300633 A | 11/2006 |
| WO | WO 2008/047405 A1 | 4/2008 |

* cited by examiner

*Primary Examiner* — Jill Warden
*Assistant Examiner* — Julie Tavares
(74) *Attorney, Agent, or Firm* — Sughrue Mion, PLLC (57) ABSTRACT

Pure water is sucked from an acid adding flow line into a syringe and discharged from a drain flow line to clean the acid adding flow line, and then a carrier gas from a gas pipe is supplied to the acid adding flow line by the syringe to dry the acid adding flow line. A sample water collecting flow line is also cleaned and dried in the same manner. A TOC measurement flow line is cleaned with cleaning water sucked from a cleaning water flow line into the syringe, then a carrier gas from the gas pipe is supplied to the TOC measurement flow line by the syringe to clean and dry a flow line through which sample water flows in an organic matter oxidative decomposition unit from the TOC measurement flow line.

5 Claims, 7 Drawing Sheets

FLOW OF CHANNEL CLEANING

Figure 5

FLOW OF PHOSPHORIC ACID ADDING CHANNEL CLEANING

Figure 6

CLEANING OF SAMPLE
COLLECTING CHANNEL

Figure 7

CLEANING OF TOC
MEASUREMENT CHANNEL

TOTAL ORGANIC CARBON MEASUREMENT APPARATUS

TECHNICAL FIELD

The present invention mainly relates to a total organic carbon (TOC) measurement apparatus for evaluating organic contamination in water with little impurity referred to as pure water or ultrapure water. Samples to be analyzed include pharmaceutical water, water used in a semiconductor manufacturing process, cooling water, boiler water, tap water, or the like.

BACKGROUND ART

A total organic carbon measurement apparatus uses either a combustion oxidation method of burning and oxidizing organic matter in a hot furnace, or a wet oxidation method of oxidizing organic matter in an organic matter oxidative decomposition unit using an ultraviolet light. The latter wet oxidation method is generally used for high-sensitive measurement of pure water or ultrapure water. The present invention is also directed to a total organic carbon measurement apparatus using the latter wet oxidation method.

As a method for measuring total organic carbon by a wet oxidation method, a known method involves providing, downstream of an organic matter oxidative decomposition unit, a carbon dioxide separation unit using a gas permeable membrane through which carbon dioxide passes, moving carbon dioxide in sample water into measurement water composed of deionized water, and measuring conductivity of the measurement water (see Patent Literature 1).

Further, there is proposed a total organic carbon measurement apparatus that uses a micromachining technique to integrate a device, thereby reducing consumption of samples or reagents and reducing elution or permeation from a pipe (see Patent Literatures 2 and 3). The total organic carbon measurement apparatus includes an organic matter oxidative decomposition unit that oxidizes organic matter in supplied sample water into carbon dioxide by ultraviolet irradiation, a carbon dioxide separation unit that moves the carbon dioxide in the sample water, which has gone through the organic matter oxidative decomposition unit, into measurement water composed of deionized water through a gas permeable membrane, and a detection unit that measures conductivity of the measurement water having gone through the carbon dioxide separation unit to obtain a carbon dioxide concentration, and at least in the carbon dioxide separation unit among the units, the sample water flows through a minute flow line formed in a chip.

In order to move the carbon dioxide in the sample water through the gas permeable membrane to the measurement water, the sample water is kept acidic so that the carbon dioxide in the sample water is gaseous. For this purpose, generally, inorganic acid containing no carbon component is added to the sample water to keep the sample water highly acidic, for example, at pH of about 2. As such acid, phosphoric acid or sulfuric acid is used.

Inorganic carbon (IC) originally dissolved in the sample water is also removed to measure a TOC concentration. For this purpose, acid is added to the sample water to be supplied to the organic matter oxidative decomposition unit, and an inorganic carbon component is removed by aeration with a carrier gas containing no carbon component, and then the sample water is supplied to the organic matter oxidative decomposition unit.

CITATION LIST

Patent Literature

[Patent Literature 1] U.S. Pat. No. 5,132,094
[Patent Literature 2] Japanese Patent Laid-Open No. 2006-300633
[Patent Literature 3] International Publication No. WO2008/047405
[Patent Literature 4] Japanese Patent Laid-Open No. 10-90134
[Patent Literature 5] Japanese Patent Laid-Open No. 2000-187027

SUMMARY OF INVENTION

Technical Problem

Such a TOC measurement apparatus is sometimes stored without being used for a long period, for example, about one month after measurement for a certain period. In this case, if a flow line for collecting the sample water or a flow line through which the sample water flows in the TOC measurement apparatus is wet with a sample, viscosity of acid added to the sample water, particularly for phosphoric acid, viscosity of the phosphoric acid remaining in the flow line is increased, which may clog the flow line. Further, the remaining sample water decays an organic component in the sample water to grow organic matter, which causes an error in a TOC measurement value when measurement is started afterward.

Generally, in an apparatus for analyzing a minor component in sample water, a flow line is usually cleaned with cleaning water after analysis is finished (see Patent Literature 4). In this case, the flow line is cleaned for preventing contamination in measurement of a next sample, and is merely cleaned with the cleaning water and not dried. This is because only cleaning is sufficient for preventing contamination, and if drying is performed, a flow line for passing a purge gas for drying is separately required.

However, with only cleaning with the cleaning water, the inside of the flow line is wet, and if the apparatus is stored unused for a long period in that state, a trace amount of organic matter remaining in the flow line may still grow.

In another analyzing apparatus, an inert gas is passed through a flow line for collecting samples in a direction opposite to a direction in sample collection after analysis is finished to dry the flow line (see Patent Literature 5). However, the inert gas in such an analyzing apparatus is not used for analysis, and thus a purge gas flow line that is not required for analysis needs to be separately provided to feed a purge gas for drying the flow line, which increases cost of the analyzing apparatus.

Thus, the present invention has an object to prevent, particularly in a TOC analyzing apparatus, acid or organic matter from remaining in a flow line by cleaning and further drying the inside of the flow line without providing a new purge gas flow line when the apparatus is stored unused for a long period after analysis is finished.

Means for Solving to Problems

A TOC measurement apparatus of the present invention includes a TOC measurement unit that measures a TOC concentration in supplied sample water, a sample introducing unit that supplies the sample water to the TOC measurement unit, and a control device that controls operations of the TOC measurement unit and the sample introducing unit.

The TOC measurement unit includes an organic matter oxidative decomposition unit that oxidizes organic matter in the supplied sample water into carbon dioxide by ultraviolet irradiation, a carbon dioxide separation unit that moves the carbon dioxide in the sample water, which has gone through the organic matter oxidative decomposition unit, into measurement water composed of deionized water through a gas permeable membrane, and a detection unit that measures conductivity of the measurement water having gone through the carbon dioxide separation unit to obtain a carbon dioxide concentration, a flow line through which sample water flows in at least the carbon dioxide separation unit being a minute flow line formed in a chip.

The sample introducing unit includes a flow line switching valve that can switch and connect a common port to each of a plurality of ports, a syringe connected to the common port of the flow line switching valve, a sample water collecting flow line that is connected to each of the plurality of ports and supplies the sample water, an acid adding flow line that supplies inorganic acid containing no carbon, a cleaning water flow line that supplies cleaning water, a TOC measurement flow line connecting to the organic matter oxidative decomposition unit, and a drain flow line opened to a drain. The syringe includes a cylinder and a piston that slides inside the cylinder, the cylinder has a distal end connected to the common port, and a base end connected to a gas pipe that supplies a carrier gas containing no carbon component into the cylinder with the piston being retracted toward the base end of the cylinder.

The control device includes a measurement unit controller that controls a conductivity measuring operation of the TOC measurement unit, a valve controller that controls an operation of the flow line switching valve, a syringe controller that controls an operation of the syringe, a sample introducing controller that controls an operation of the sample introducing unit via the valve controller and the syringe controller, a storage cleaning button for instructing cleaning for storage with the acid adding flow line and the sample water collecting flow line being each set to suck pure water, and storage cleaning means for performing cleaning and drying steps (A), (B) and (C) below via the valve controller and the syringe controller when storage cleaning is instructed from the storage cleaning button.

(A) An operation of sucking pure water from the acid adding flow line into the syringe and discharging the pure water from the drain flow line to clean the acid adding flow line, and then supplying the carrier gas from the gas pipe to the acid adding flow line by the syringe to dry the acid adding flow line.

(B) An operation of sucking pure water from the sample water collecting flow line into the syringe and discharging the pure water from the drain flow line to clean the sample water collecting flow line, and then supplying the carrier gas from the gas pipe to the sample water collecting flow line by the syringe to dry the sample water collecting flow line.

(C) An operation of sucking cleaning water from the cleaning water flow line into the syringe and supplying the cleaning water from the TOC measurement flow line to the flow line through which the sample water flows in the organic matter oxidative decomposition unit to clean the flow line through which the sample water flows in the organic matter oxidative decomposition unit, and then supplying the carrier gas from the gas pipe to the flow line through which the sample water flows in the organic matter oxidative decomposition unit by the syringe to dry the flow line through which the sample water flows in the organic matter oxidative decomposition unit.

The storage cleaning refers to performing cleaning for long-period storage.

An example of inorganic acid containing no carbon supplied from the acid adding flow line is phosphoric acid. A phosphoric acid solution is increased in viscosity when dried, which may clog a minute flow line. Thus, application of the present invention has particular significance. Other examples of the acid may include sulfuric acid.

Among the steps (A), (B) and (C), the step (A) is first performed. A subsequent step may be (B) or (C). Specifically, the order of steps is (A)→(B)→(C) or (A)→(C)→(B).

In the step (C), when the flow line through which the sample water flows in the organic matter oxidative decomposition unit is cleaned with cleaning water, an ultraviolet ray may be applied to the flow line. Thus, even if organic matter remains in the flow line, the organic matter is decomposed by the ultraviolet ray, thereby eliminating organic matter.

Also in the step (C), after the flow line through which the sample water flows in the organic matter oxidative decomposition unit is cleaned, a distal end of the cleaning water flow line on a side of a cleaning water container may be opened so that the flow line through which the sample water flows in the organic matter oxidative decomposition unit and also the cleaning water flow line are dried. This can also dry the cleaning water flow line.

Advantageous Effects of Invention

In the present invention, when it is known that the apparatus will not be used for a long period after analysis is finished, the storage cleaning means is activated to clean, with pure water, the acid adding flow line, the sample water collecting flow line, and the TOC measurement flow line and the flow line through which the sample water flows in the oxidative decomposition unit, thereby removing acid or organic matter adhering to the flow lines, and then drying the flow lines with the carrier gas. This prevents clogging of the flow line or growth of organic matter even if the apparatus is stored for a long period. In particular, the flow line through which the sample water flows in the oxidative decomposition unit is a minute flow line formed in a chip, and clogging of this flow line is prevented. Further, the gas pipe that supplies the carrier gas for drying is originally provided in the sample introducing unit for use in measurement by the TOC measurement apparatus, and there is no need to separately provide a carrier gas pipe for drying.

DESCRIPTION OF EMBODIMENTS

Figure 1:
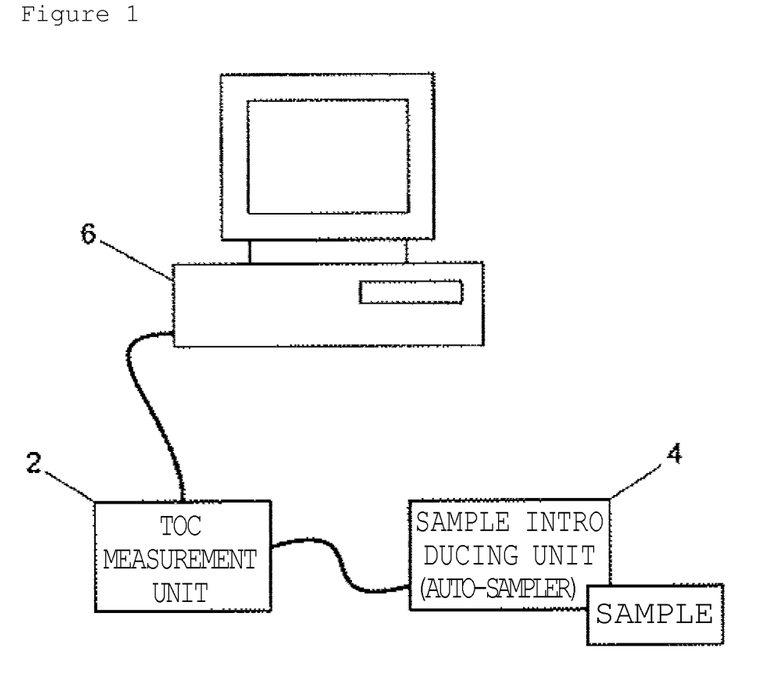
FIG. 1 is a schematic view of an embodiment.

FIG. 1 schematically shows an embodiment of a TOC measurement apparatus in its entirety. To a TOC measurement unit 2, an auto-sampler as a sample introducing unit 4 is connected, and sample water is automatically collected and supplied to the TOC measurement unit 2. A personal computer as a control device 6 is connected in order to control operations of the TOC measurement unit 2 and the sample introducing unit 4. The control device 6 is not limited to the personal computer, but may be a dedicated microprocessor for the TOC measurement apparatus.

Figure 2:
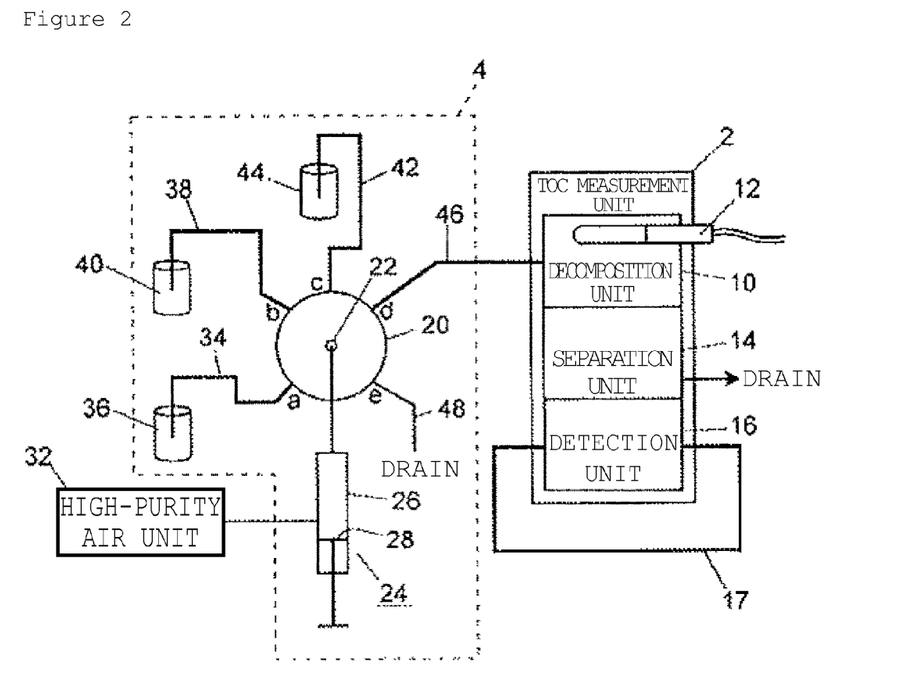
FIG. 2 is a block diagram showing a configuration of the embodiment.

FIG. 2 shows detailed configurations of the TOC measurement unit 2 and the sample introducing unit 4. The TOC measurement unit 2 includes an organic matter oxidative decomposition unit 10, a carbon dioxide separation unit 14, and a detection unit 16.

The organic matter oxidative decomposition unit 10 oxidizes organic matter in sample water supplied from the sample introducing unit 4 via a TOC measurement flow line 46 into carbon dioxide by ultraviolet irradiation from an ultraviolet lamp 12 such as a mercury lamp.

The carbon dioxide separation unit 14 moves the carbon dioxide in the sample water, which has gone through the organic matter oxidative decomposition unit 10, into measurement water composed of deionized water through a gas permeable membrane.

A flow line through which the sample water flows in the carbon dioxide separation unit 14 is a minute flow line formed in a chip. When the organic matter oxidative decomposition unit 10, the carbon dioxide separation unit 14, and the detection unit 16 are integrated into a chip, a flow line through which the sample water flows in the organic matter oxidative decomposition unit 10 is also a minute flow line formed in a chip. If the TOC measurement unit 2 is left for a long period with phosphoric acid remaining in the minute flow line through which the sample water flows, the phosphoric acid may be increased in viscosity to clog the flow line.

The detection unit 16 measures conductivity of the measurement water having gone through the carbon dioxide separation unit 14 to obtain a carbon dioxide concentration. The detection unit 16 is provided with a circulation flow line 17 that absorbs the carbon dioxide moved from the carbon dioxide separation unit 14 via the gas permeable membrane, and supplies deionized water used as measurement water for detecting conductivity of the measurement water. The circulation flow line 17 is shown in a simplified manner, but includes ion exchange resin. The measurement water whose conductivity is detected by the detection unit 16 is reprocessed with the ion exchange resin and reused as measurement water.

The TOC measurement unit 2 may have a specific structure described in Patent Literature 2 or 3.

The sample introducing unit 4 includes a flow line switching valve 20 that can switch and connect a common port 22 to each of a plurality of ports. An 8-port valve is used as the flow line switching valve 20. In this embodiment, not all of the 8 ports are used, and thus a 6-port valve may be used. A syringe 24 is connected to the common port 22 of the flow line switching valve. A sample water collecting flow line 34 connecting to a sample container 36 is connected to a port a of the plurality of ports, and sample water can be sucked from the sample water collecting flow line 34 into the syringe 24. The sample water collecting flow line 34 can also directly suck water in lines such as a semiconductor production process so that the TOC measurement apparatus can be used for on-line measurement. In order to add phosphoric acid as inorganic acid containing no carbon to the sample water, an acid adding flow line 38 connecting to a phosphoric acid cartridge 40 is connected to a port b, and the phosphoric acid is sucked from the phosphoric acid cartridge 40 through the acid adding flow line 38 into the syringe 24. A cleaning water flow line 42 connecting to a cartridge or bottle 44 containing pure water or deionized water as cleaning water is connected to a port c, and the cleaning water is sucked from the cleaning water container 44 into the syringe 24. The TOC measurement flow line 46 that connects to the organic matter oxidative decomposition unit 10 and supplies the sample water to the organic matter oxidative decomposition unit 10 is connected to a port d. A drain flow line 48 opened to a drain is connected to a port e.

The syringe 24 includes a cylinder 26 and a piston 28 that slides inside the cylinder 26, the cylinder 26 has a distal end connected to the common port e, and a base end connected to a carrier gas supply flow line 30 that supplies carrier gas containing no carbon component into the cylinder 26 with the piston 28 being retracted toward the base end of the cylinder 26. The carrier gas supply flow line 30 supplies, as a carrier gas, high-purity air from which carbon dioxide is removed and contained in a gas canister 32. The carrier gas is used as a sparge gas for removing inorganic carbon (IC) in TOC measurement, and is provided for original analysis purpose in the TOC measurement apparatus. In the present invention, the carrier gas is used for purging the flow line.

Figure 3:
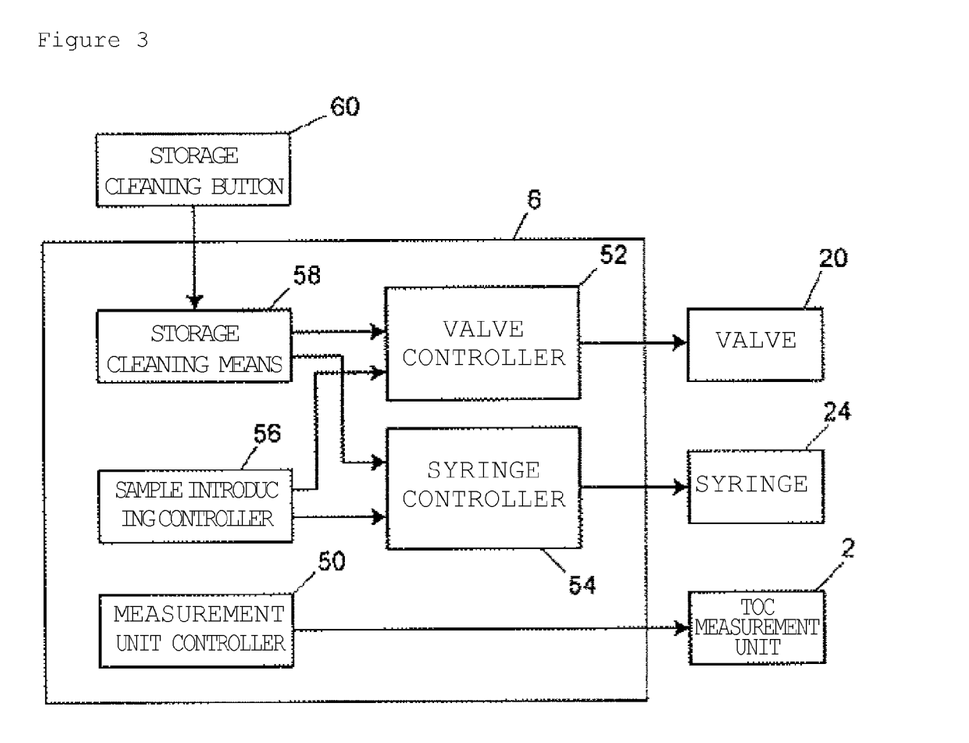
FIG. 3 is a block diagram of a control device in the embodiment.

As shown in FIG. 3, the control device 6 includes a measurement unit controller 50 that controls a conductivity measuring operation of the TOC measurement unit 2, a valve controller 52 that controls an operation of the flow line switching valve 20, a syringe controller 54 that controls an operation of the syringe 24, a sample introducing controller 56 that controls an operation of the sample introducing unit 4 via the valve controller 52 and the syringe controller 54, a storage cleaning button 60 for instructing cleaning for storage with the acid adding flow line 38 and the sample water collecting flow line 34 being each set to suck pure water, and storage cleaning means 58 for performing cleaning and drying steps via the valve controller 52 and the syringe controller 54 when storage cleaning is instructed from the storage cleaning button 60. The storage cleaning button 60 is a keyboard or a button displayed on a display screen, and used to activate the storage cleaning means 58.

First, a procedure for the TOC measurement by the TOC measurement apparatus of the embodiment in FIG. 2 will be described. The valve 20 connects the sample water collecting flow line 34 and the syringe 24, and the piston 28 of the syringe 24 is retracted toward the base end to collect a certain amount of sample water into the syringe 24. Then, the valve 20 is switched to connect the syringe 24 and the phosphoric acid adding flow line 38, and the piston 28 is further retracted to suck phosphoric acid into the syringe 24. The phosphoric acid is added so that the sample water is highly acidic at pH of about 2. Then, the valve 20 is switched to connect the syringe 24 and the drain flow line 48. In this state, when the piston 28 is closer to the base end than a connecting position between the carrier gas supply flow line 30 and the syringe 24, the piston 28 is kept in the position, and if the piston 28 is closer to the distal end than the connecting position between the carrier gas supply flow line 30 and the syringe 24, the piston 28 is retracted so as to be closer to the base end than the connecting position between the carrier gas supply flow line 30 and the syringe 24. In this state, the carrier gas is supplied from the gas canister 32 into the syringe 24 to aerate a mixed liquid of the sample water and the phosphoric acid collected in the syringe, thereby discharging inorganic carbon originally dissolved in the sample water to the drain.

Then, the supply of the carrier gas is stopped, the valve 20 is switched to connect the syringe 24 and the TOC measurement flow line 46, and a certain amount of sample water in the syringe 24 is supplied to the TOC measurement unit 2. In the TOC measurement unit 2, the ultraviolet lamp 12 is turned on, and organic matter in the sample water is decomposed into carbon dioxide by ultraviolet irradiation while the sample water is passing through the decomposition unit 10. The carbon dioxide in the sample water is gaseous because the phosphoric acid is added to the sample water and the sample water is acidic. The sample water having gone through the decomposition unit 10 is introduced into the separation unit 14. In the separation unit 14, the sample water is in contact with deionized water as measurement water via a gas permeable membrane, and thus moves through the gas permeable membrane into the measurement water. Conductivity of the measurement water introduced from the separation unit 14 to the detection unit 16 is measured by a conductivity meter of the detection unit 16. The measurement water has natural conductivity of deionized water before movement of the carbon dioxide, the movement of the carbon dioxide increases conductivity, and a TOC concentration of the sample water is obtained based on a change in the conductivity.

A relationship between the TOC concentration of the sample water and the conductivity measured by the detection unit 16 can be easily obtained by previously performing measurement with this apparatus using a standard sample to prepare a calibration curve.

Also in a general measurement operation, when measurement of one sample is finished, cleaning water is sucked from the cleaning water flow line 42 into the syringe 24, the cleaning water is pushed out from the syringe 24 to the TOC measurement flow line 46 to clean a sample water flow line in the decomposition unit 10 from the TOC measurement flow line 46.

Next, with reference to FIGS. 4 to 7, an operation of storage cleaning in the case where the apparatus is not used for a long period will be described.

Figure 4:
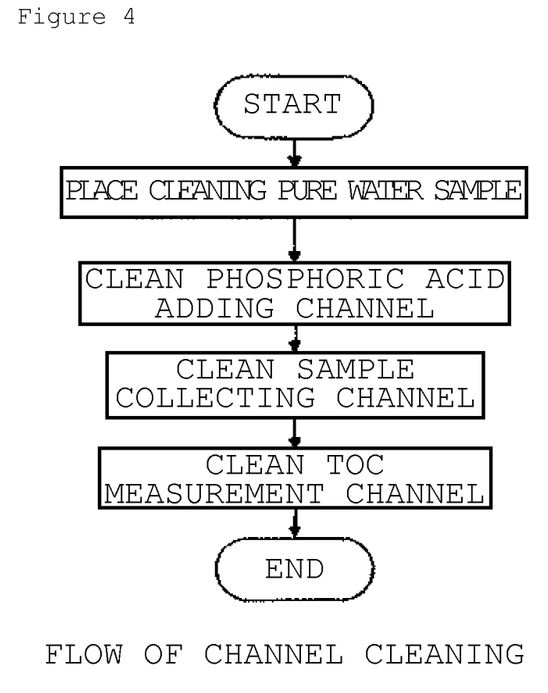
FIG. 4 is a flowchart showing an entire cleaning operation in the embodiment.

Before the storage cleaning, the sample container 36 at a distal end of the sample water collecting flow line 34 is removed and replaced by a container of pure water for cleaning, and the phosphoric acid cartridge 40 at a distal end of the acid adding flow line 38 is also removed and replaced by a container of pure water for cleaning. Then, the storage cleaning button 60 is used to activate the storage cleaning means 58. When the storage cleaning means 58 is activated, cleaning is performed according to a predetermined sequence.

FIG. 4 shows an entire flow of the storage cleaning. As a sequence of cleaning, the phosphoric acid adding flow line 38 is first cleaned. This is because the phosphoric acid adding flow line 38 is dirtiest. Then, the sample water collecting flow line 34 and the TOC measurement flow line 46 are cleaned, and either may be cleaned first. In FIG. 4, the sample water collecting flow line 34 is first cleaned, and then the TOC measurement flow line 46 is cleaned.

Figure 5:
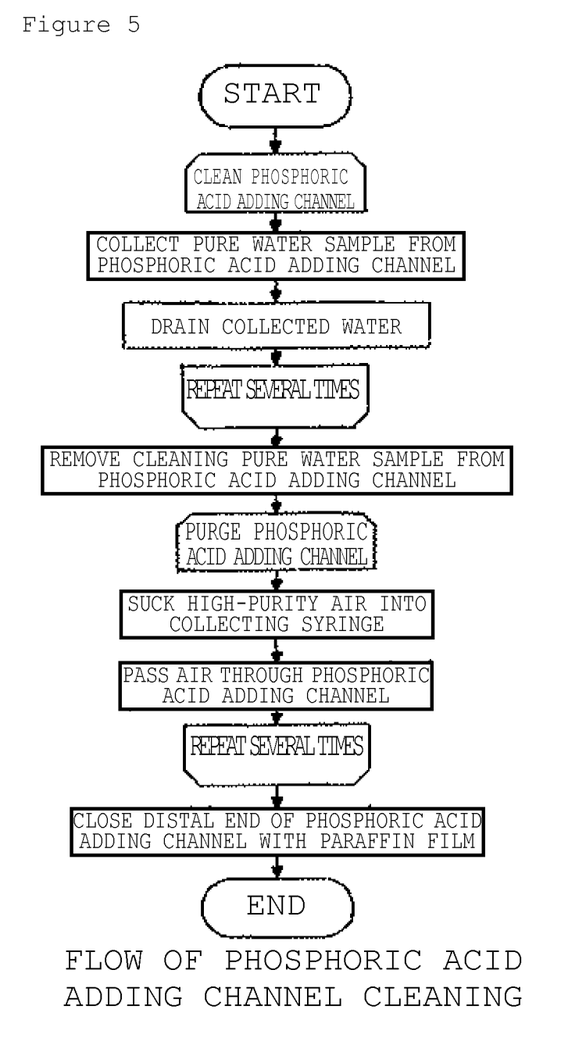
FIG. 5 is a flowchart showing a cleaning operation of a phosphoric acid adding flow line in the embodiment.

FIG. 5 shows a cleaning step of the phosphoric acid adding flow line 38. The valve 20 connects the phosphoric acid adding flow line 38 and the syringe 24 to collect pure water from the phosphoric acid adding flow line 38 into the syringe 24. Then, the valve 20 is switched to connect the syringe 24 and the drain flow line 48 to discharge cleaning water collected in the syringe 24 to the drain. The step of sucking the cleaning water through the phosphoric acid adding flow line 38 and discharging the cleaning water to the drain is repeated a plurality of times, for example, three to five times.

Then, the container for cleaning water connected to the phosphoric acid adding flow line 38 is removed to open the distal end of the phosphoric acid adding flow line 38 to the atmosphere. With the syringe 24 and the drain flow line 48 being connected, the piston 28 of the syringe 24 is retracted so as to be closer to the base end than the connecting position between the carrier gas flow line and the syringe 24 to suck the carrier gas into the syringe 24. Then, the valve is switched to connect the syringe 24 and the phosphoric acid adding flow line 38, the carrier gas in the syringe 24 is fed to and passed through the phosphoric acid adding flow line 38 to dry the inside of the phosphoric acid adding flow line 38. The step of sucking the carrier gas into the syringe 24 and passing the carrier gas through the phosphoric acid adding flow line 38 is repeated a plurality of times, for example, three to five times. This dries the inside of the phosphoric acid adding flow line 38, and then the distal end of the phosphoric acid adding flow line 38 is closed by a paraffin film to prevent entry of outside air.

Figure 6:
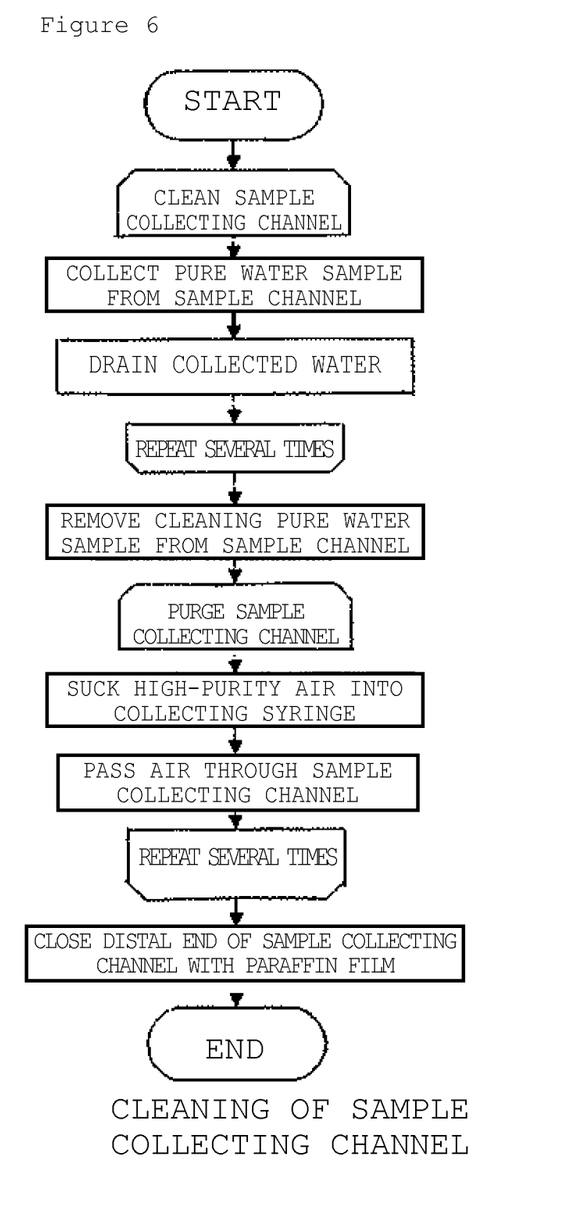
FIG. 6 is a flowchart showing a cleaning operation of a sample water collecting flow line in the embodiment.

FIG. 6 shows a cleaning step of the sample water collecting flow line 34. The valve 20 connects the sample water collecting flow line 34 and the syringe 24 to collect pure water from the sample water collecting flow line 34 into the syringe 24. Then, the valve 20 is switched to connect the syringe 24 and the drain flow line 48 to discharge cleaning water collected in the syringe 24 to the drain. The step of sucking the cleaning water through the sample water collecting flow line 34 and discharging the cleaning water to the drain is repeated a plurality of times, for example, three to five times.

Then, the container for cleaning water connected to the sample water collecting flow line 34 is removed to open a distal end of the sample water collecting flow line 34 to the atmosphere. With the syringe 24 and the drain flow line 48 being connected, the piston 28 of the syringe 24 is retracted so as to be closer to the base end than the connecting position between the carrier gas flow line and the syringe 24 to suck the carrier gas into the syringe 24. Then, the valve is switched to connect the syringe 24 and the sample water collecting flow line 34, the carrier gas in the syringe 24 is fed to and passed through the sample water collecting flow line 34 to dry the inside of the sample water collecting flow line 34. The step of sucking the carrier gas into the syringe 24 and passing the carrier gas through the sample water collecting flow line 34 is repeated a plurality of times, for example, three to five times. This dries the inside of the sample water collecting flow line 34, and then the distal end of the sample water collecting flow line 34 is closed by a paraffin film to prevent entry of outside air.

Figure 7:
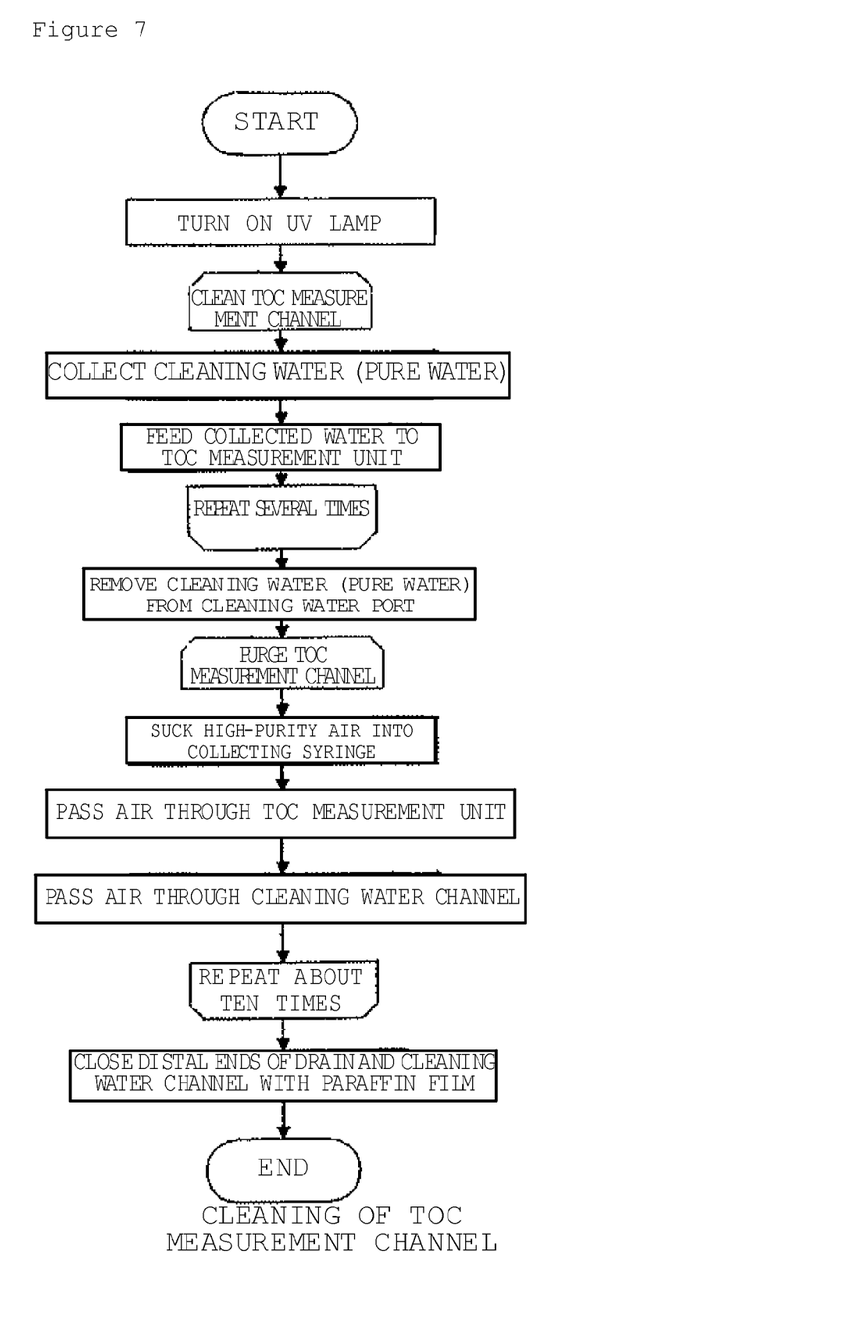
FIG. 7 is a flowchart showing a cleaning operation of a TOC measurement flow line in the embodiment.

FIG. 7 shows a cleaning step of the flow line through which the sample water flows in the decomposition unit 10 from the TOC measurement flow line 46. This cleaning step is performed with the ultraviolet lamp 12 in the decomposition unit 10 being turned on. The valve 20 connects the cleaning water flow line 42 and the syringe 24 to collect cleaning water into the syringe 24. The valve 20 is switched to connect the syringe 24 and the TOC measurement flow line 46, and the collected cleaning water is passed from the TOC measurement flow line 46 to the flow line through which the sample water flows in the decomposition unit 10. This step is repeated a plurality of times, for example, three to five times.

Then, the cleaning water container 44 is removed from the cleaning water flow line 42, and the gas is passed through the cleaning water flow line 42 and the TOC measurement flow line 46 to dry the cleaning water flow line 42 and the TOC measurement flow line 46. This method is the same as the method for drying other flow lines. The carrier gas is sucked into the syringe 24 and passed through the sample water flow line in the decomposition unit 10 from the TOC measurement flow line 46, and the valve 20 is switched to also pass the carrier gas through the cleaning water flow line 42. The passing of the carrier gas through the cleaning water flow line 42 and the TOC measurement flow line 46 is repeated about 10 times. This dries the TOC measurement flow line 46 and the sample water flow line in the decomposition unit 10, and the cleaning water flow line 42. Then, a distal end of the sample water flow line in the decomposition unit 10 and a distal end of the cleaning water flow line 42 are closed by a paraffin film.

Thus, the flow lines through which the sample water flows in the sample introducing unit 4 and the TOC measurement unit 2 are all cleaned and dried, and the distal ends are closed so as to prevent entry of outside air. Thus, the apparatus is ready for a long-period storage.

REFERENCE SIGNS LIST

- 2 TOC measurement unit
- 4 sample introducing unit
- 6 control device
- 10 organic matter oxidative decomposition unit
- 14 carbon dioxide separation unit
- 16 detection unit
- 20 flow line switching valve
- 22 common port
- 24 syringe
- 34 sample water collecting flow line
- 38 phosphoric acid adding flow line
- 42 cleaning water flow line
- 46 TOC measurement flow line
- 48 drain flow line
- 50 measurement unit controller
- 52 valve controller
- 54 syringe controller
- 56 sample introducing controller
- 58 storage cleaning means
- 60 storage cleaning button

What is claimed is:

1. A total organic carbon measurement apparatus comprising:
    a total organic carbon measurement unit including an organic matter oxidative decomposition unit that oxidizes organic matter in supplied sample water into carbon dioxide by ultraviolet irradiation, a carbon dioxide separation unit that moves the carbon dioxide in the sample water, which has gone through the organic matter oxidative decomposition unit, into measurement water composed of deionized water through a gas permeable membrane, and a detection unit that measures conductivity of the measurement water having gone through the carbon dioxide separation unit to obtain a carbon dioxide concentration, a flow line through which sample water flows in at least the carbon dioxide separation unit being a minute flow line formed in a chip;
    a sample introducing unit including a flow line switching valve that can switch and connect a common port to each of a plurality of ports, a syringe connected to the common port of the flow line switching valve, a sample water collecting flow line that is connected to each of the plurality of ports and supplies the sample water, an acid adding flow line that supplies inorganic acid containing no carbon, a cleaning water flow line that supplies cleaning water, a TOC measurement flow line connecting to the organic matter oxidative decomposition unit, and a drain flow line opened to a drain, the syringe including a cylinder and a piston that slides inside the cylinder, the cylinder having a distal end connected to the common port, and a base end connected to a gas pipe that supplies a carrier gas containing no carbon component into the cylinder with the piston being retracted toward the base end of the cylinder; and
    a control device including a measurement unit controller that controls a conductivity measuring operation of the total organic carbon measurement unit, a valve controller that controls an operation of the flow line switching valve, a syringe controller that controls an operation of the syringe, a sample introducing controller that controls an operation of the sample introducing unit via the valve controller and the syringe controller, a storage cleaning button for activating a storage cleaning means for instructing cleaning for storage with the acid adding flow line and the sample water collecting flow line being each set to suck pure water each from a pure water source and each of the flow lines is connected to a pure water source, and the storage cleaning means for performing cleaning and drying steps (A), (B) and (C) below via the valve controller and the syringe controller when storage cleaning is instructed from the storage cleaning button:
    (A) an operation of sucking pure water from the acid adding flow line into the syringe and discharging the pure water from the drain flow line to clean the acid adding flow line, and then supplying the carrier gas from the gas pipe to the acid adding flow line by the syringe to dry the acid adding flow line;
    (B) an operation of sucking pure water from the sample water collecting flow line into the syringe and discharging the pure water from the drain flow line to clean the sample water collecting flow line, and then supplying the carrier gas from the gas pipe to the sample water collecting flow line by the syringe to dry the sample water collecting flow line; and
    (C) an operation of sucking cleaning water from the cleaning water flow line into the syringe and supplying the cleaning water from the TOC measurement flow line to the flow line through which the sample water flows in the organic matter oxidative decomposition unit to clean the flow line through which the sample water flows in the organic matter oxidative decomposition unit, and then supplying the carrier gas from the gas pipe to the flow line through which the sample water flows in the organic matter oxidative decomposition unit by the syringe to dry the flow line through which the sample water flows in the organic matter oxidative decomposition unit.

2. The total organic carbon measurement apparatus according to claim 1, wherein the acid adding flow line supplies phosphoric acid.

3. The total organic carbon measurement apparatus according to claim 2, wherein the storage cleaning means, the valve controller and syringe controller are programmed to perform the cleaning in the sequence, the step (A) is first performed, then one of the steps (B) and (C) is performed, and the other of the steps (B) and (C) is finally performed.

4. The total organic carbon measurement apparatus according to claim 1, an ultraviolet light provided in the oxidative decomposition unit.

5. The total organic carbon measurement apparatus according to claim 1, the storage means, the valve controller and the syringe controller are programmed to perform the cleaning in the sequence wherein in the step (C), after the flow line through which the sample water flows in the organic matter oxidative decomposition unit is cleaned, a distal end of the cleaning water flow line on a side of a cleaning water container is opened so that the flow line through which the sample water flows in the organic matter oxidative decomposition unit is dried and also the cleaning water flow line is cleaned.

* * * * *